United States Patent [19]

Ogura et al.

[11] Patent Number: 4,898,970

[45] Date of Patent: Feb. 6, 1990

[54] PROCESS FOR PRODUCING FLUORINATED ESTERS

[75] Inventors: Eiji Ogura; Kunihiro Mito; Shoji Arai, all of Shinnanyo, Japan

[73] Assignees: Onoda Cement Co., Ltd., Onoda; Tosoh Corporation, Shinnanyo, both of Japan

[21] Appl. No.: 463,020

[22] Filed: Feb. 1, 1983

[30] Foreign Application Priority Data

Feb. 5, 1982 [JP] Japan .................................. 57-17128

[51] Int. Cl.$^4$ .................... C07C 67/11; C07C 69/003; C07C 69/14
[52] U.S. Cl. .................................... 560/236; 260/408; 560/87; 560/111; 560/180; 560/197
[58] Field of Search ................ 560/87, 180, 111, 236, 560/197; 260/408

[56] References Cited

U.S. PATENT DOCUMENTS

| | | | |
|---|---|---|---|
| 2,658,086 | 11/1953 | Ruh et al. | 570/174 |
| 2,868,846 | 1/1959 | Lawlor et al. | 560/236 |
| 3,418,360 | 12/1968 | Schulz et al. | 560/236 |
| 4,360,469 | 11/1982 | Dietl et al. | 260/396 R |

*Primary Examiner*—Vivian Garner
*Attorney, Agent, or Firm*—Oblon, Spivak, McClelland, Maier & Neustadt

[57] ABSTRACT

This invention relates to a process for producing a fluorinated ester containing a trifluoromethyl group by esterification in the presence of γ-butyrolactone as a solvent, and more particularly a process or producing a fluorinated ester containing a trifluoromethyl group which is useful as a raw material of various fluorine containing compound.

5 Claims, No Drawings

PROCESS FOR PRODUCING FLUORINATED ESTERS

BACKGROUND OF THE INVENTION

1. Field of the Invention

This invention relates to a process for producing a fluorinated ester containing a trifluoromethyl group and more particularly to a process for producing a fluorinated ester containing a trifluoromethyl group, in which 1,1,1-trifluoro-2-halogenated ethane is esterified by a specified carboxylic acid salt, dicarboxylic acid salt or dicarboxylic acid salt having an ether-bonding in molecule using a γ-butyrolactone solvent.

1,1,1-Trifluoro-2-halogenated ethane is useful as a raw material of various fluorine-containing compounds. However, 1,1,1-trifluoro-2-chloroethane ($CF_3CH_2Cl$) or 1,1,1-trifluoro-2-bromoethane ($CF_3CH_2Br$), a class of 1,1,1-trifluoro-2-halogenated ethanes is extremely tough in C—Cl bonding or C—Br bonding and one may encounter much difficulty to hydrolyze them to synthesize 2,2,2-trifluoroethanol.

2. Description of the Prior Art

There is described in U.S. Pat. No. 2,868,846 a process for preparing 2,2,2-trifluoroethanol, in which $CF_3CH_2Cl$ is reacted with an alkali metal salt of acetic acid in a solvent having hydroxyl groups, such as ethylene glycol. However, it hardly seems that this process is satisfactory from an industrial view point, because the reaction temperature is high to cause a thermal degradation of glycols constituting the solvent, a corrosion of structural materials of the reaction vessel and further to result in an occurrence of side reactions and so on with the product formation.

It is considered that the following two step reactions take place to give $CF_3CH_2OH$ in the reactions of the above mentioned U.S. patent, where $CH_3COOK$ is used as an example:

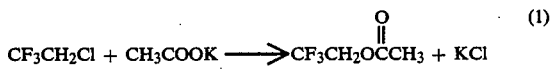

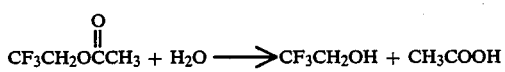

It is also considered that the esterification reaction of the (1) equation is the rate determing step while the (2) reaction rapidly proceeds.

SUMMARY OF THE INVENTION

The inventors considered that if it is possible to easily convert $CF_3CH_2Cl$ or $CF_3CH_2Br$ into a carboxylic acid ester at the first step it can be easily carried out to synthesize fluorinated compounds, for example, $CF_3CH_2OH$ and the like from the carboxylic acid ester used as an intermediate raw material. As the result of the investigation, it is found that a reaction, in which $CF_3CH_2Cl$ or $CF_3CH_2Br$ is reacted with a specified carboxylic acid salt, dicarboxylic acid salt or dicarboxylic acid having an ether-bonding in molecule in the γ-butyrolactone used as a solvent, easily give a corresponding carboxylic acid ester, that is, a fluorinated ester containing a trifluoromethyl group. These findings lead the inventors to the present invention.

DETAILED DESCRIPTION OF THE INVENTION

This invention provides a process for producing a fluorinated ester containing a trifluoromethyl group, in which 1,1,1-trifluoro-2-halogenated ethane and a member or a mixture of at least two members of (1) a carboxylic acid salt represented by the formula

wherein R is an alkyl group having a carbon number of not more than 19 or a phenyl group, and M is Na, K or Mg;

(2) a dicarboxylic acid salt represented by the formula

wherein B is an alkylene group having a carbon number of 0 to 8 or a phenylene group, and M and M' are Na, K or Mg, which can be identical to or different from each other; and (3) a dicarboxylic acid salt having an ether-bonding in molecule, which is represented by the formula

wherein R and R' are alkylene groups having a summed up carbon number of not more than 10, and M and M' are Na, K or Mg, which can be identical to or different from each other are subjected to an esterification reaction in γ-butyrolactone used as the solvent.

Examples of the carboxylic acid salt, dicarboxylic acid salt, which can be used but which are not limiting are as follows:

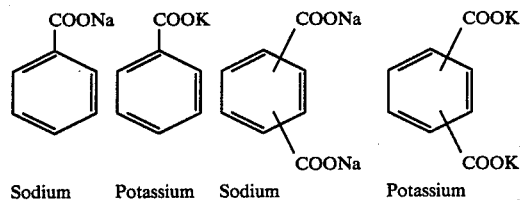

| Sodium benzoate | Potassium benzoate | Sodium Phthalateate | Potassium Phthalateate | oxalates and the like.

In a case in which the above mentioned formula MOOCROR'COOM is $MOOC(CH_2)_3O(CH_2)_3COOM'$, γ-butyrolactone can be used for the reaction after it is reacted with a member of or a mixture of at least two members of KOH, NaOH, $K_2CO_3$, $Na_2CO_3$, $NaHCO_3$ and $KHCO_3$ to produce $MOOC(CH_2)_3O(CH_3)_2COOM'$. The molar ratio of γ-buiyrolactone used as the solvent and the 1,1,1-trifluoro-2halogenated ethane (γ-butyrolactone/1,1,1-trifluoro-2-halogenated ethane) is not less than 0.5 and not more than 20, preferably not less than 0.8 and not more than 15.

The solvent effect of γ-butyrolactone is not sufficient to in a case, in which the molar ratio is less than 0.5 but the ratio more than 20 is uneconomical because the amount of γ-butyrolactone to be recovered remarkably increases in such a case.

The molar ratio of the member of or the mixture of members of the above mentioned carboxylic acid salt and dicarboxylic acid salt and the 1,1,1-trifluoro-2-halogenated ethane (carboxylic acid salt/1,1,1-trifluoro- 2-halogenated ethane) is not less than 0.5 and not more than 10. The reaction temperature is not lower than 130° C. and not higher than 250° C., preferably not lower than 140° C. and not higher than 230° C. In a case, in which the reaction temperature is lower than 130° C., the reaction rate is slow. This necessitates a considerably long reaction time. On the other hand, the reaction temperature higher than 250° C. results in disadvantages such as increase in side-reactions and degradation of γ-butyrolactone. The reaction pressure may be of a generated pressure due to the raw materials and product substances (self-generated pressure). The reaction pressure may also be one pressurized by an inert gas such as nitrogen and the like, which does not affect the reaction, so as to give a pressure not more than 40 kg/cm$^2$G at room temperature before the initiation of the reaction.

In addition to the above description, Examples are stated below which will aid in understanding this invention. However, the scope of this invention is not restricted to these Examples.

EXAMPLES

EXAMPLE 1

Predetermined amounts of γ-butyrolactone and potassium acetate were charged into a 200 ml capacity autoclave made of a structural material of SUS304, which was provided with a magnetic stirrer and the autoclave was closed. The system was aspirated by vacuum and $CF_3CH_2Br$ which was previously gathered in a glass pressure vessel was introduced into the autoclave through a conduct pipe. After that, the content of the autoclave was pressurized by air to 2 Kg/cm$^2$G and heated to 150° C. in an electric furnace with stirring to react them for 4 hours. After completion of the reaction, gas components released from the autoclave were collected in a trap cooled by a dry ice-methanol. Subsequently, the autoclave was opened and the reaction solution was recovered by n-propanol used as a washing solvent which was previously cooled to 0° C. Produced gas components and the reaction solution was analyzed and determined by the gas chromatography using methylisobutylketone as an internal standard substance.

The water content of γ-butyrolactone used in this example was determined by the Karl-Fisher method to give 0.1% by weight.

Used amounts of the raw materials, recovered amounts of the reaction products and unreacted raw materials are shown in Table 1.

EXAMPLE 2

Predetermined amounts of γ-butyrolactone and sodium acetate were charged into a 5000 ml capacity autoclave made of a structural material of SUS304, which was provided with a magnetic stirrer and the autoclave was sealed. Air of the system was substituted with nitrogen by repeating 4 times operations of first pressurizing by nitrogen to 4 Kg/cm$^2$G and subsequently purging nitrogen. $CF_3CH_2Cl$ which was previously gathered in a pressure vessel was introduced into the autoclave through a conduct pipe. After that, the content of the autoclave was pressurized by nitrogen to 4 Kg/cm$^2$G and heated to 225° C. with stirring in an electric furnace to react them for 4 hours.

After completion of the reaction, gas components released from the autoclave were collected in a trap cooled by a dry ice-methanol. Subsequently, the autoclave was opened and the contents were quickly filtered by a glass filter to separate unreacted sodium acetate and formed sodium chloride from the reaction solution. The collected sodium acetate and sodium chloride were repeatedly washed with γ-butyrolactone and the resulting washing solution was gathered into the reaction solution.

The gas components and reaction solution, which were recovered in these operation were analyzed and determined by the gas chromatography using dioxane as a internal standard substance.

Results are shown in Table 1.

EXAMPLE 3

The reaction was carried out in the same manner as in Example 2 except for using potassium acetate and conducting the reaction at 200° C.

Results are shown in Table 1.

EXAMPLE 4

The reaction was carried out in the same manners as in Example 1 except for using $CF_3CH_2Cl$ and potassium benzoate and conducting the reaction at 200° C.

Results are shown in Table 1.

EXAMPLE 5

The reaction was carried out in the same manner as in Example 1 except for using $CF_3CH_2Cl$ and potassium oleate, excluding the pressurization by air and conducting the reaction at 225° C. for 3 hours.

Results are shown in Table 1.

EXAMPLE 6

The reaction was carried out in the same manner as in Example 1 except for using $CF_3CH_2Cl$ and $O[(CH_2)_3COOK]_2$ (a potassium salt of bis-(3-carboxypropyl) ether) and conducting the reaction at 200° C.

Results are shown in Table 1.

EXAMPLE 7

The reaction was carried out in the same manners as in Example 1 except for using $CF_3CH_2Cl$ and potassium phthalate, excluding the pressurization by air and conducting the reaction at 200° C.

Results are shown in Table 1.

EXAMPLE 8

The reaction was carried out in the same manners as in Example 1 except for using $CF_3CH_2Cl$ and potassium succinate, excluding the pressurization by air and conducting the reaction at 200° C.

Results are shown in Table 1.

TABLE 1

|  |  | Example 1 | Example 2 | Example 3 | Example 4 | Example 5 | Example 6 | Example 7 | Example 8 |
|---|---|---|---|---|---|---|---|---|---|
| Charged Amount of raw Material (mol.) | Reagent for hydrolysis | $CH_3COOK$ | $CH_3COONa$ | $CH_3COOK$ | $C_6H_5COOK$ | $C_{17}H_{33}COOK$ | $O[(CH_2)_3CO_2K]_2$ | ⌬-COOK (o-COOK) | ⌬-CH$_2$COOK (o-CH$_2$COOK) |
|  |  | 0.200 | 7.00 | 7.01 | 0.139 | 0.120 | 0.097 | 0.200 | 0.154 |
|  | $CF_3CH_2Br$ | 0.114 |  |  |  |  |  |  |  |
|  | $CF_3CH_2Cl$ |  | 7.14 | 7.04 | 0.147 | 0.119 | 0.217 | 0.202 | 0.202 |
|  | γ-butyrolactone | 1.57 | 34.5 | 34.3 | 1.39 | 1.39 | 1.39 | 1.39 | 1.39 |
| Amount Recovered (mol.) | Unreacted $CF_3CH_2Br$ | 0.005 |  |  |  |  |  |  |  |
|  | Unreacted $CF_3CH_2Cl$ |  | 1.89 | 0.40 | 0.010 | 0.015 | 0.061 | 0.040 | 0.048 |
|  | Ester | $CF_3CH_2OOCCH_3$ | $CF_3CH_2OOCCH_3$ | $CF_3CH_2OOCCH_3$ | $C_6H_5COOCH_2CF_3$ | $C_{17}H_{33}COOCH_2CF_3$ | $O[(CH_2)_3CO_2CH_2CF_3]_2$ | ⌬-COOCH$_2$CF$_3$ (o-COOCH$_2$CF$_3$) | ⌬-CH$_2$COOCH$_2$CF$_3$ (o-CH$_2$COOCH$_2$CF$_3$) |
|  |  | 0.077 | 3.94 | 4.98 | 0.128 | 0.080 | 0.053 | 0.057 | 0.051 |
|  | $CF_3CH_2OH$ | 0.016 | 0.214 | 0.476 | 0.004 | 0.005 | 0.006 | 0.006 | 0.009 |
| Reaction Condition | Reaction Temperature (°C.) | 150 | 225 | 200 | 200 | 225 | 200 | 200 | 200 |
|  | Reaction Time (hrs) | 4 | 4 | 4 | 4 | 3 | 4 | 4 | 4 |

We claim:
1. A process for producing a fluorinated ester containing a trifluoromethyl group, which comprises:
subjecting a 1,1,1-trifluoro-2-halogenated ethane of the formula

$$CF_3CH_2X$$

wherein X is Cl or Br, in γ-butyrolactone used as a solvent, to an esterification reaction with at least one carboxylic acid selected from the group consisting of
(1) a carboxylic acid salt of the formula $$RCOOM$$

wherein
R is an alkyl group having a carbon number of not more than 19 or a phenyl group, and
M is Na, K, or Mg;
(2) a dicarboxylic acid salt represented by the general formula
MOOCRCOOM' wherein
R is $C_0$–$C_8$ alkylene group or a phenylene group, and
M and M' are Na, K or Mg, which may be the same or different; and (3) a dicarboxylic acid salt having an ether-bond in molecule, of the formula $$MOOCROR'COOM'$$

wherein
R and R' are $C_1$ to $C_{10}$ alkylene groups which may be the same or different, and
M and M' are the same or different and are Na, K or Mg.

2. The process for producing the fluorinated ester containing the trifluoromethyl group as set forth in claim 1, wherein the molar ratio of γ-butyrolactone to the 1,1,1-trifluoro-2-halogenated ethane is 0.5 to 20.

3. The process for producing the fluorinated ester containing the trifluoromethyl group as set forth in claim 1 or 2, wherein the molar ratio of the member or the mixture of the at least two member of the carboxylic acid salt, the dicarboxylic acid salt and the dicarboxylic acid salt containing an ether-bonding in molecule, to the 1,1,1-trifluoro-2-halogenated ethane ia 0.5 to 10.

4. The process for producing the fluorinated ester containing the trifluoromethyl group as set forth in any one of claims 1 or 2, wherein the reaction temperature is 130° to 250° C.

5. The process for producing the fluorinated ester containing the trifluoromethyl group as set forth in any one of claims 1 or 2, wherein the carboxylic acid salt is acetate.

* * * * *

UNITED STATES PATENT AND TRADEMARK OFFICE
CERTIFICATE OF CORRECTION

PATENT NO. : 4,898,970

DATED : FEBRUARY 6, 1990

INVENTOR(S) : Eiji OGURA et al

It is certified that error appears in the above-identified patent and that said Letters Patent is hereby corrected as shown below:

Column 2, line 19, "B" should read -- R --;

line 55, ")$_3$O(CH$_3$)$_2$COOM' " should read

-- )$_3$O(CH$_2$)$_3$COOM' --;

line 55, "buiyrolactone" should read

-- butyrolactone --.

Column 8, claim 3, line 21, "ia" should read --is--.

Signed and Sealed this

Fifth Day of May, 1992

*Attest:*

DOUGLAS B. COMER

*Attesting Officer*     *Acting Commissioner of Patents and Trademarks*